(12) United States Patent
Hsiung et al.

(10) Patent No.: US 6,236,075 B1
(45) Date of Patent: May 22, 2001

(54) ION SENSITIVE TRANSISTOR (75) Inventors: Shen-Kan Hsiung, Chung-Li; Jung-Chuan Chou, Yunlin Hsien; Tai-Ping Sun; Wen Yaw Chung, both of Chung-Li; Hung-Kwei Liao, Hsichu Hsien; Chung-Lin Wu, Taipei, all of (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/266,420

(22) Filed: Mar. 10, 1999

(30) Foreign Application Priority Data

Nov. 20, 1998 (TW) .................................................. 87119298

(51) Int. Cl.[7] .................................................. H01L 23/58
(52) U.S. Cl. .................. 257/252; 257/253; 257/414; 438/49; 204/411; 204/412; 204/419
(58) Field of Search .................... 257/253, 252, 257/414; 438/49; 204/411, 412, 419

(56) References Cited

U.S. PATENT DOCUMENTS

| 4,397,714 | * | 8/1983 | Janata et al. | 204/1 T |
| 4,792,836 | * | 12/1988 | Quinlan | 357/30 |
| 5,319,226 | | 6/1994 | Sohn et al. | 257/253 |
| 5,466,348 | * | 11/1995 | Holm-Kennedy | 204/153.1 |
| 5,520,787 | * | 5/1996 | Hanagan et al. | 204/409 |
| 5,798,556 | * | 8/1998 | Hughes et al. | 257/414 |
| 5,851,489 | * | 12/1998 | Wolf et al. | 422/82.02 |

* cited by examiner

*Primary Examiner*—William Mintel
(74) *Attorney, Agent, or Firm*—Price And Gess (57) ABSTRACT

The present invention discloses a method of forming a metal layer by thermal evaporation or RF reactive sputtering in order to fabricate a light shielding layer for an ion sensitive field effect transistor. The multi-layered construction of the ion sensitive field effect transistor with a metal thin film as a light shielding layer is $SnO_2$/metal/$SiO_2$ or $SnO_2$/metal/$Si_3N_4$/$SiO_2$, and is able to lower the effect of light successfully.

10 Claims, 9 Drawing Sheets

FIG. 6B

ION SENSITIVE TRANSISTOR

BACKGROUND OF THE INVENTION

1. Field of the Invention

The present invention relates to an ion sensitive field effect transistor, and more particularly to the formation of a thin metal film by thermal evaporation or RF reactive sputtering as a method of fabricating a light shielding layer for an ion sensitive field effect transistor.

2. Description of the Related Art

A conventional ion transistor, for example a glass electrode, has good stability and can choose ions accurately. However, it is large and expensive, and its reaction time is lengthy. Therefore, the advanced technology of the silicon semiconductor integration circuit for ion sensitive field effect transistors will eventually replace the glass electrode.

In 1970, Piet Bergveld removed the metal film of the general MOS transistor above the gate and put it into an ion solution. As the solution changed in the concentration of $H^+$, the oxide layer above the gate acted as an ion sensitive film and caused the voltage of the interface between the film and the solution to change. Further the amount of current through the channel changed. By the way of measuring the changing amount of current, it was possible to measure the concentration of $H^+$ and the other ions. Thus, Piet Bergveld called his research the ion sensitive field effect transistor.

In the 1970's, the process and application of ion sensitive field effect transistors were in a research stage, while in the 1980's, the study of ion sensitive field effect transistors included not only basic theory, but also advanced into practical application. In fact, over 30 kinds of ion sensitive field effect transistors used to measure the ions and chemical materials were developed. The ion sensitive field effect transistors decreased in size and improved in design and function. Further, they had characteristics that the conventional ion transistor didn't have such as:

1. Small size, allowing the measurement of the ion concentration of a smaller amount of solution;
2. High input resistance and low output resistance;
3. Quick response; and
4. Process compatibility with MOS field effect transistors.

Figure 1:
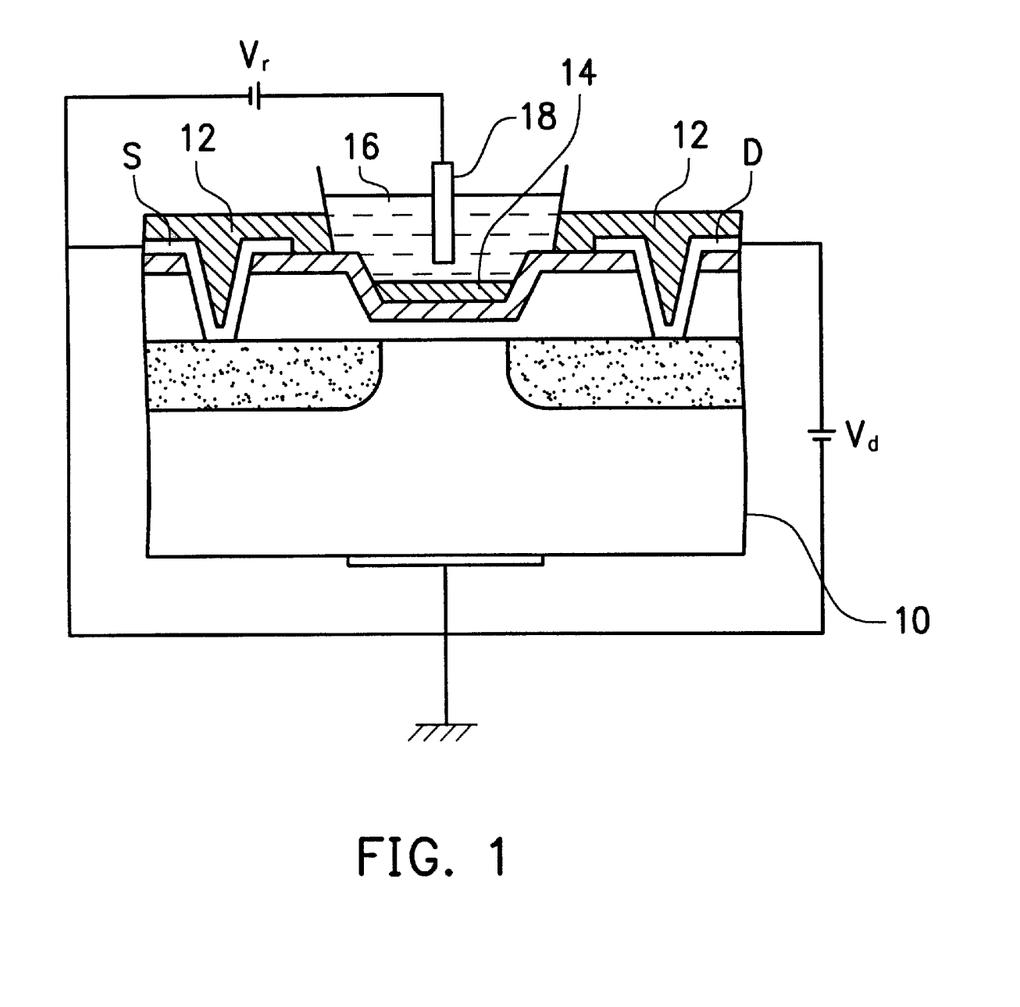
FIG. 1 shows a cross-sectional view of a conventional ion sensitive field effect transistor.

However, there are two points that need to be overcome for the practical application of ion sensitive field effect transistors. One is the effect of temperature, and the other is the influence of surrounding light while measuring. Regarding the first point, the effect of temperature can be lowered by means of complementary circuits. U.S. Pat. No. 5,319,226 (Jun. 7, 1994) discloses an ion sensitive field effect transistor in which the formation of a $Ta_2O_5$ thin film above the gate of ion sensitive field effect transistor results in the construction $Ta_2O_5/Si_3N_4/SiO_2$. With reference to FIG. 1, the construction of the ion sensitive field effect transistor and its operation can be specifically realized.

As shown in FIG. 1, the construction and operation of this kind of transistor comprise: forming a transistor having a drain D and a source S by ion implantation in a semiconductor substrate 10; forming a $Si_3N_4/SiO_2$ isolating layer 12 above the drain and the source; utilizing RF reactive sputtering to form a $Ta_2O_5$ thin film 14 above the gate isolating portion. After this, the $Ta_2O_5$ thin film 14 contacts the solution 16 directly so as to react with the hydrogen and changes its concentration. Accordingly, the voltage on the surface of the $Ta_2O_5$ thin film 14 changes, and the amount of current through the drain changes. Therefore, the pH measurement can be obtained by detecting the drain voltage Vd, where the drain voltage Vd represents an opposed voltage to a reference voltage Vr, while the reference voltage Vr is defined by a reference electrode 18 that contacts the solution 16.

Regarding the influence of light, the materials used in sensing membrane, for example $Si_3N_4$, $Ta_2O_5$, $Al_2O_3$, and $SnO_2$, are materials whose energy bands are wide (over 3.5 eV). Accordingly, light will go through these membranes, form electron-hole pairs, and cause errors in the measurement. Therefore, when using this kind of transistor, it is possible to be sure that the measurement is accurate only if the light intensity of the measuring environment is constant.

SUMMARY OF THE INVENTION

Accordingly, the primary object of the present invention is to provide a method for fabricating an ion sensitive field effect transistor in which the sensing element can be effectively shielded from the influence of light, thereby increasing the accuracy of the measurement of the ion concentration.

The present invention achieves the above-indicated object by providing an ion sensitive field effect transistor with a metal membrane to serve as a light shielding layer. After the formation of a conventional ion sensitive field effect transistor, aluminum wire on tungsten wire is melted by thermal evaporation onto the $SiO_2/Si_3N_4$ membrane with a metal mask, thereby forming a metal membrane to serve as a light shielding layer. $SnO_2$ is then deposited on the metal of the gate by thermal evaporation or RF sputtering to form a sensing membrane capable of sensing the ion concentration.

BRIEF DISCRIPTION OF THE DRAWINGS

These and other features of the present invention will now be described in detail with reference to the accompany drawings, in which.

DESCRIPTION OF PREFERRED EMBODIMENT

Figure 2A:
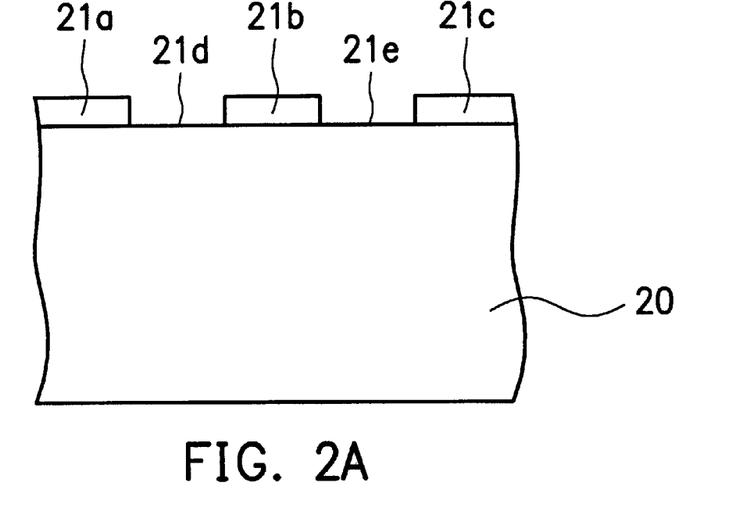
FIGS. 2A–2H show cross-sectional views of the fabricating process of a preferred embodiment according to the invention.

Referring to FIG. 2A, a p-type semiconductor substrate 20 is provided (in this embodiment, a wafer with a four-inch diameter). In the diagrams of the embodiment, the shape of the semiconductor substrate 20 is planar in order to simplify the graph. After the process of cleaning the wafer, a $SiO_2$ layer is formed on the semiconductor substrate 20 by wet oxidation, the thickness of the layer being about 500 nm. Patterning layers 21a, 21b, 21c, and the openings 21d, 21e are formed on the $SiO_2$ layer by a photolithography or an etching process (for example, wet etching).

Figure 2B:
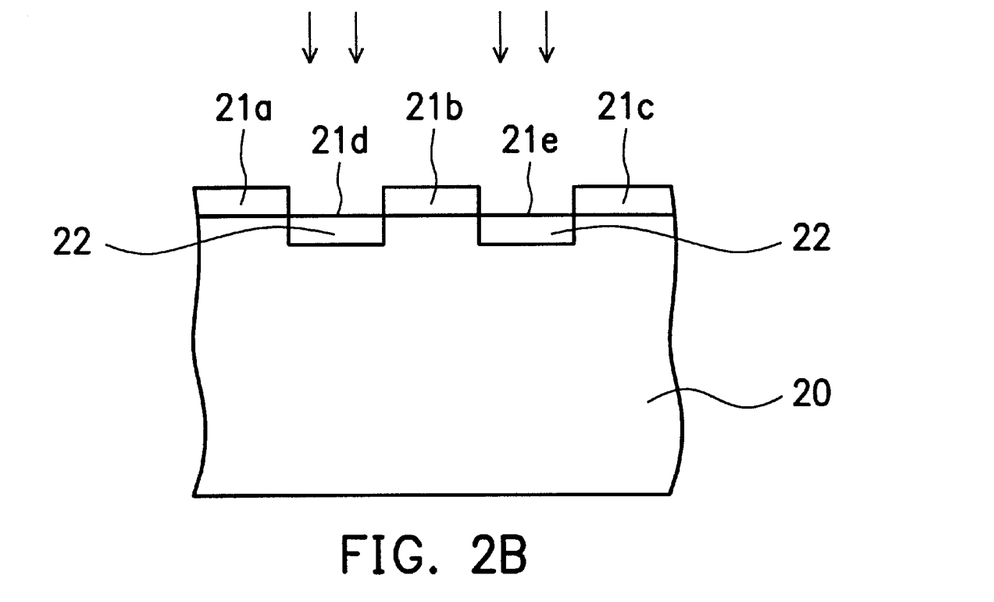

Referring to FIG. 2B, ions are implanted in the openings of the semiconductor substrate 20 in order to form a pair of isolating source/drains 22.

Figure 2C:
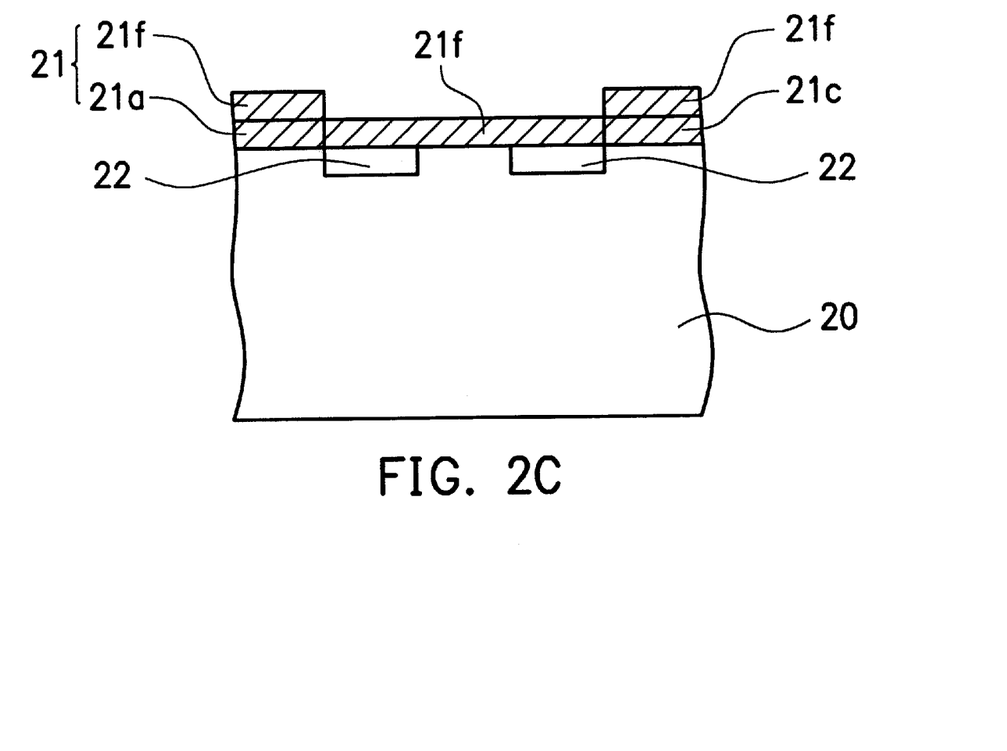

Referring to FIG. 2C, the $SiO_2$ layer 21b is removed by a photolithography step or an etching process, e.g., wet oxidation. A $SiO_2$ layer 21f with a thickness of about 100 nm is formed on the $SiO_2$ layers 21a, 21c and on the surface of the semiconductor substrate 20 between the $SiO_2$ layers 21a and 21c by dry oxidation. In order to explain the embodiment more clearly, the $SiO_2$ layers 21a, 21c and 21f are combined and represented by a $SiO_2$ layer 21.

Figure 2D:
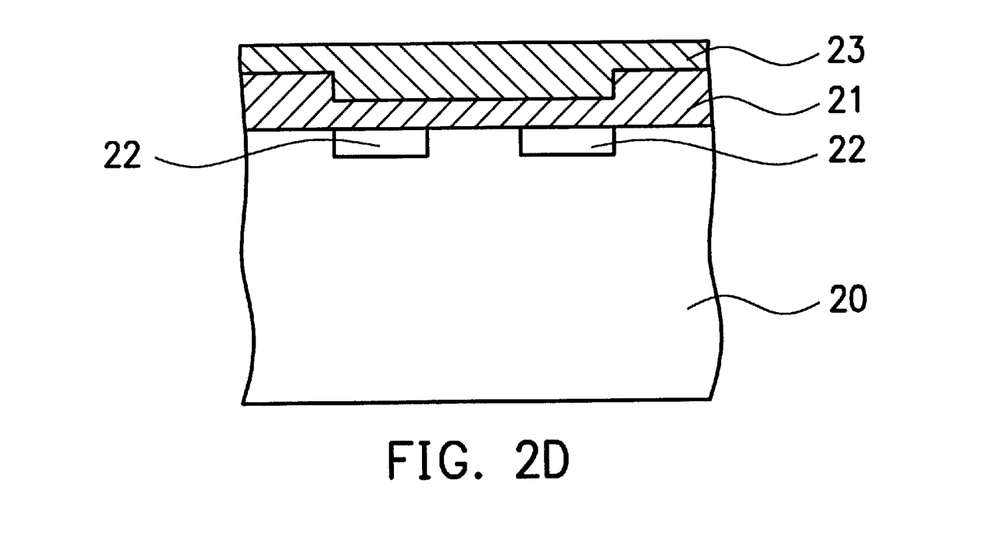

Referring to FIG. 2D, a layer of $Si_3N_4$ 23 is formed above the $SiO_2$ layer 21 with a thickness of about 100 nm.

Figure 2E:
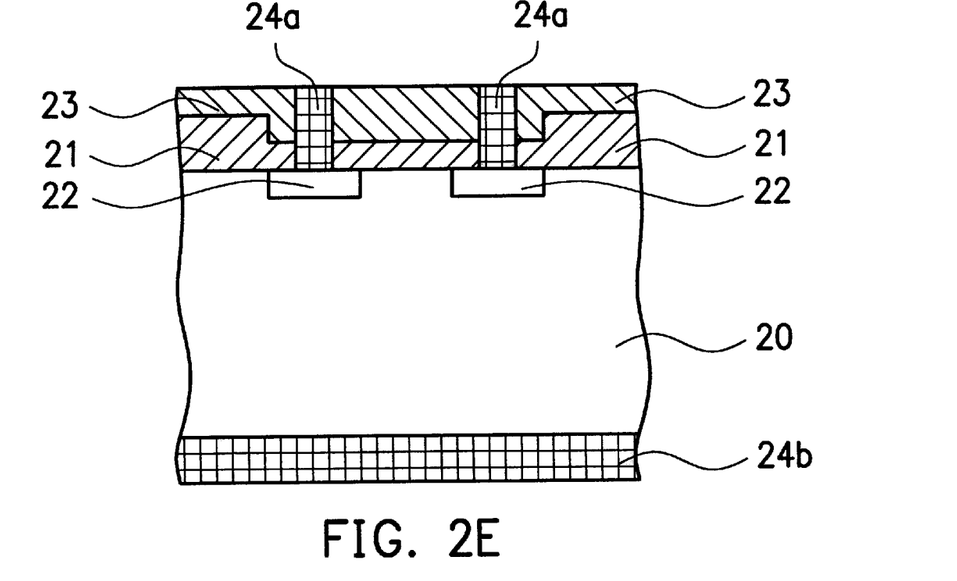

Referring to FIG. 2E, the $Si_3N_4$ layer 23 and the $SiO_2$ layer 21 above the source/drain are etched to form a pair of contact holes by photolithography and anisotropic etching. Then, aluminum is sputtered on the surface of the $Si_3N_4$ layer 23 and the contact holes. After that, the aluminum is etched back and a pair of aluminum plugs 24a are formed. In addition, an aluminum layer 24b is sputtered under the semiconductor substrate 20.

Figure 2F:
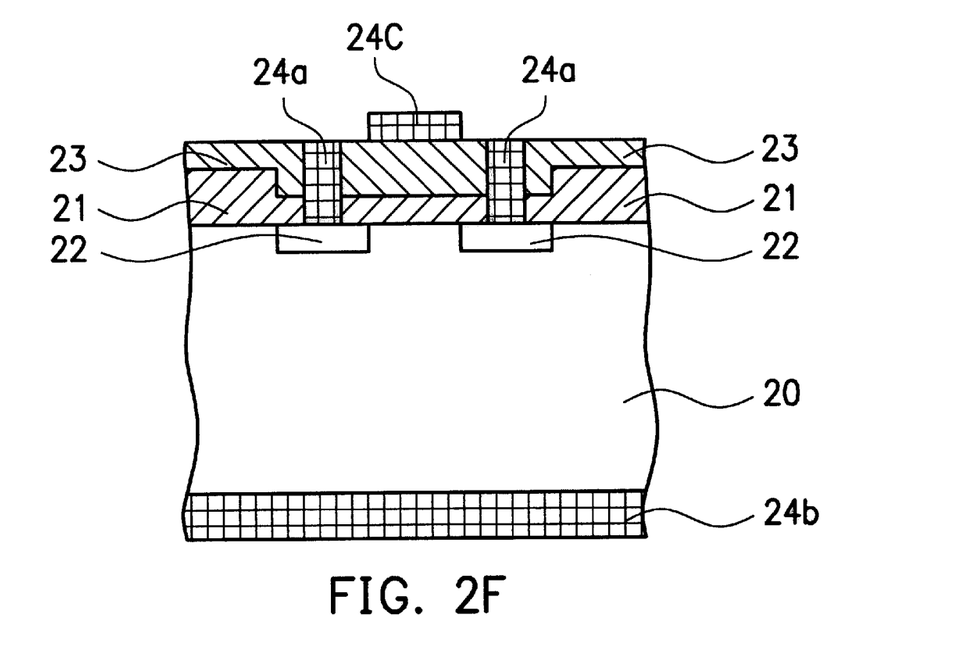

Referring to FIG. 2F, an aluminum wire (diameter=1 mm) and a tungsten wire is melted by thermal evaporation onto the surface of $Si_3N_4$ layer 23 with a metal mask (3000 $\mu m*3000 \mu m$). A current of about 10~15 A, but preferably 15 A, is transmitted through the transistor, and a low pressure of $10^{-5}$~$10^{-6}$ torr, but preferably $10^{-6}$ torr, is maintained in the environment. The transistor is then evaporated for about 20 minutes so as to form an aluminum layer 24c to act as the light shielding layer.

Figure 2G:
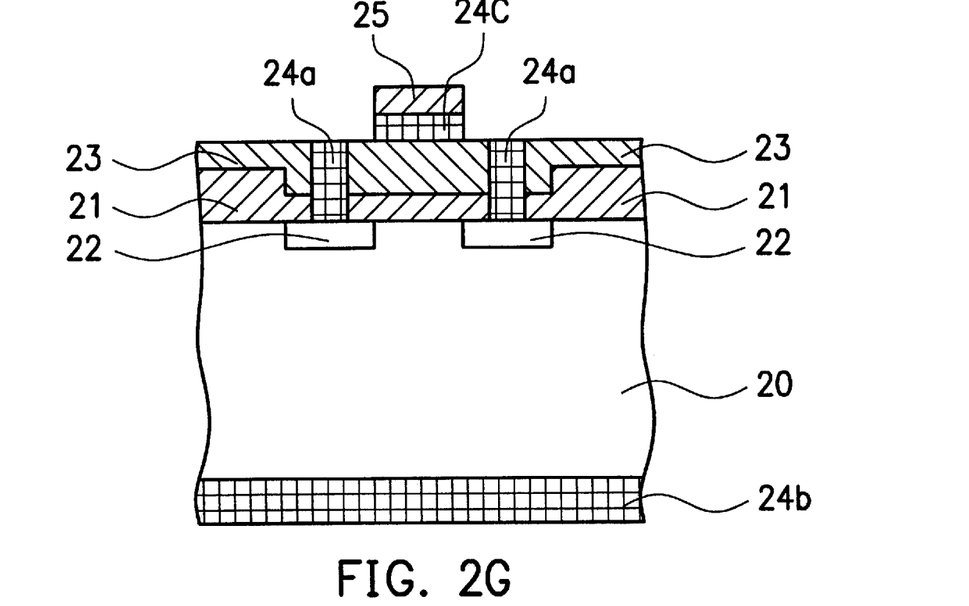

Referring to FIG. 2G, a $SnO_2$ thin film 25 of 150~200 nm thickness is formed above the aluminum layer 24c by RF sputtering.

Figure 2H:
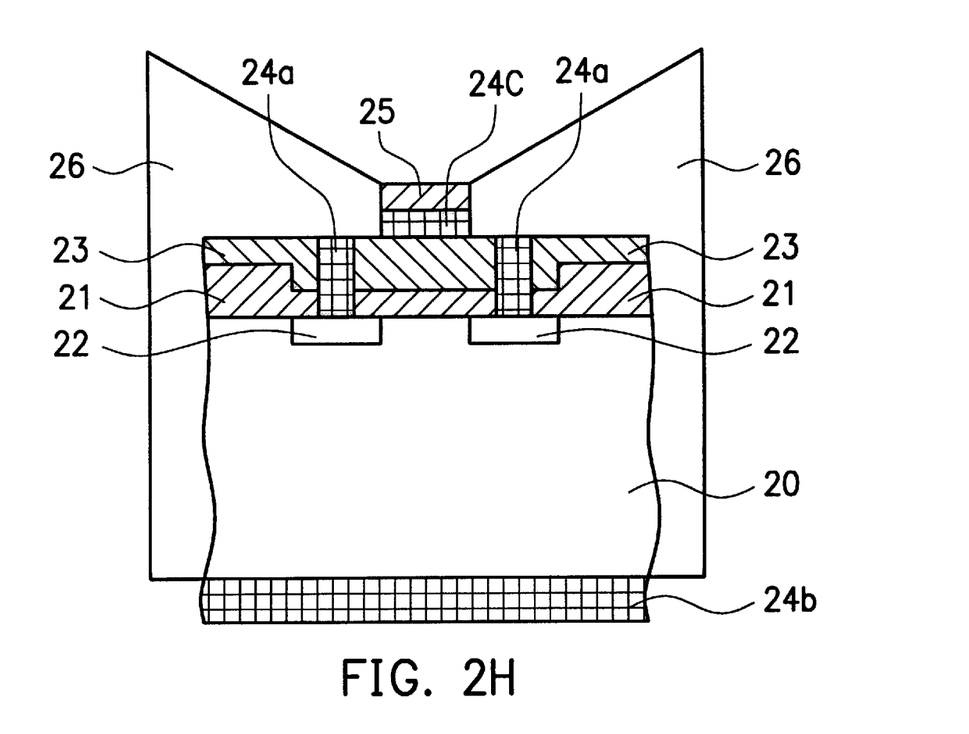

Last, as shown in FIG. 2H, the entire element except for the gate sensing membrane is coated with epoxy resin 26 and put in an oven that is about 150° C. and heated about 15 minutes for curing. Accordingly, an ion sensitive field effect transistor that has a metal thin film as a light shielding layer is successfully fabricated.

Figure 3:
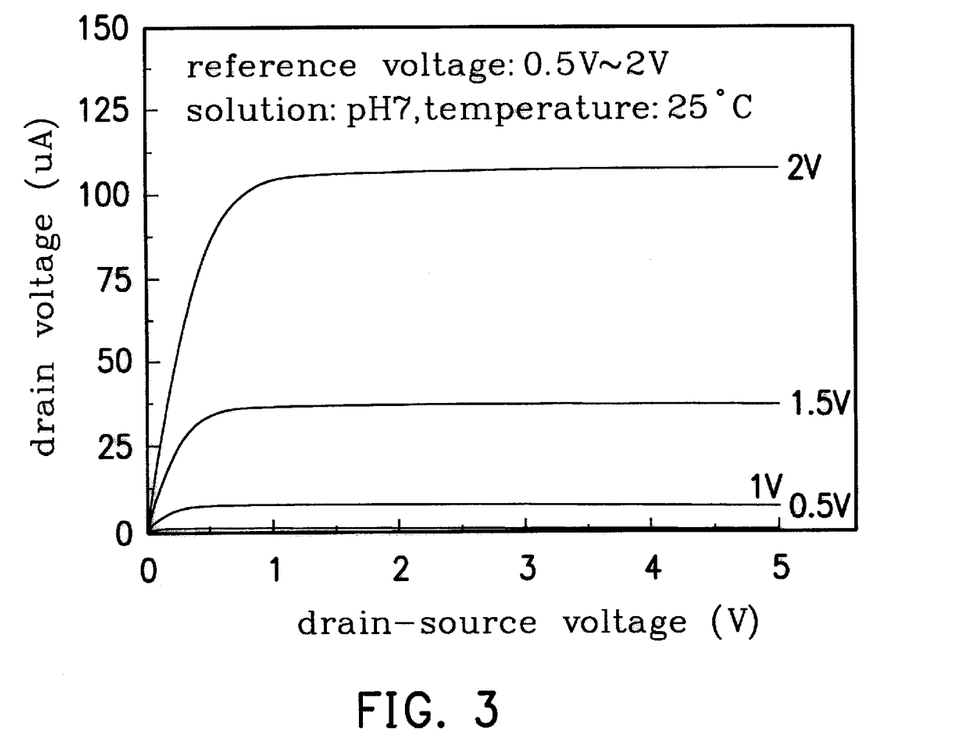
FIG. 3 shows the electrical characteristics of the preferred embodiment according to the invention.

As shown in FIG. 3, the curves showing the electric characteristics of the ion sensitive field effect transistor that has the metal thin film as a light shielding layer are the same as the characteristic curves of the output of a junction field effect transistor when the voltage between the drain and the source is lower than 5 volts and the drain current is lower than 150 $\mu A$.

Figure 4:
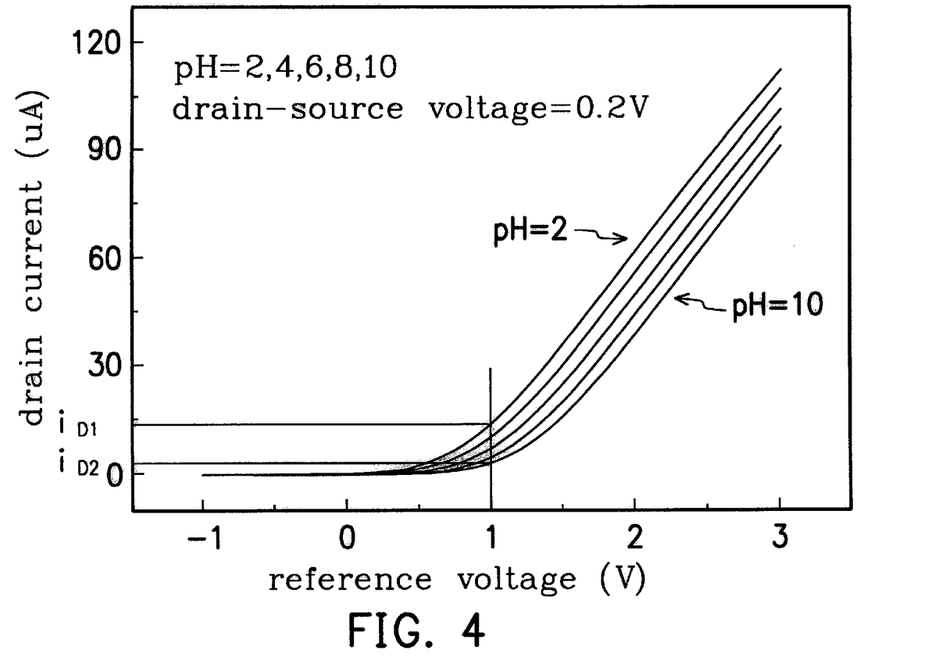
FIG. 4 shows the sensing characteristics of the preferred embodiment according to the invention.

Referring to FIG. 4, as shown in the curves, if the reference voltage is fixed at 1 volt, the on current of the drain of the transistor $i_{D1}$ corresponding to the pH value 10 is higher than $i_{D2}$ corresponding to the pH value 2. Therefore, when the voltage between the drain and the source is controlled at 0.2 volts, the measurement of the on current of the drain $i_D$ results in the pH(pOH) value. Thus, the concentration of the hydrogen ions is known.

Figure 5A:
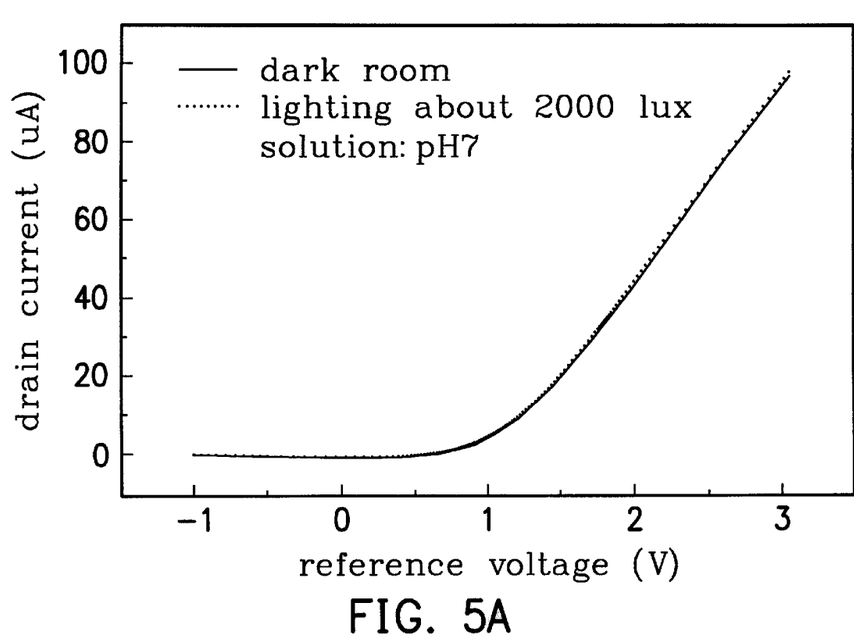
FIG. 5A shows the comparison of the sensing characteristics in a dark room and in room lit to about 2000 lux of the preferred embodiment according to the invention.
Figure 5B:
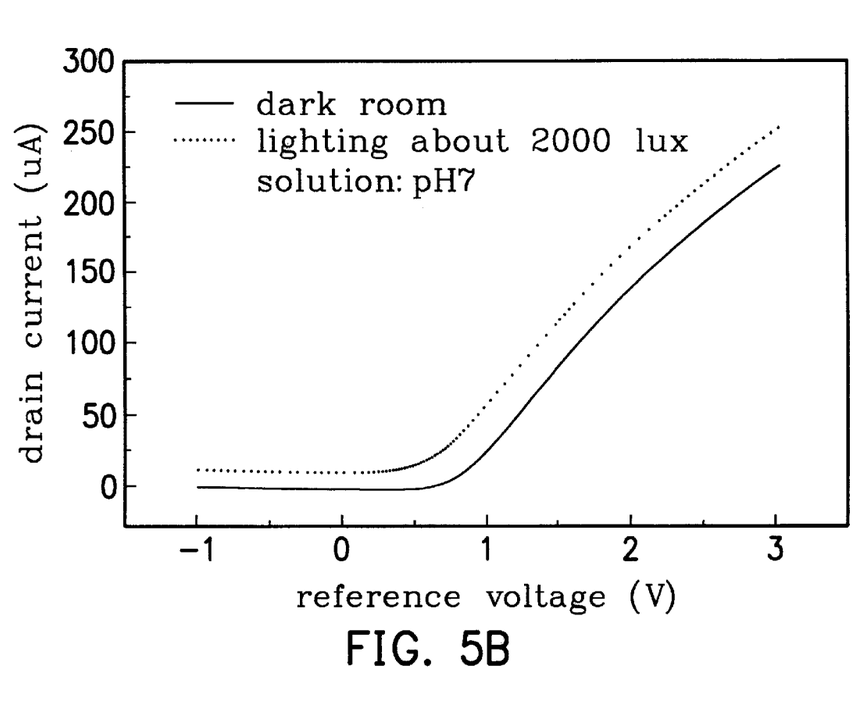
FIG. 5B shows the comparison of sensing characteristics in dark and in lighting about 2000 lux of the conventional ion sensitive field effect transistor.

Referring to FIG. 5A, it is apparent that the characteristic curves of the present invention when measuring in dark room and in a room lit with twenty-fold the general intensity of normal room light almost match. This means that the metal shielded layer of the ion sensitive field effect transistor can lower the influence of the light. Compared with FIG. 5A, however, the two characteristic curves of FIG. 5B of the conventional ion sensitive field effect transistor are different in dark room and in a lit room. This means that the measuring results of the conventional ion sensitive field effect transistor are not as accurate as those of the present invention.

Figure 6A:
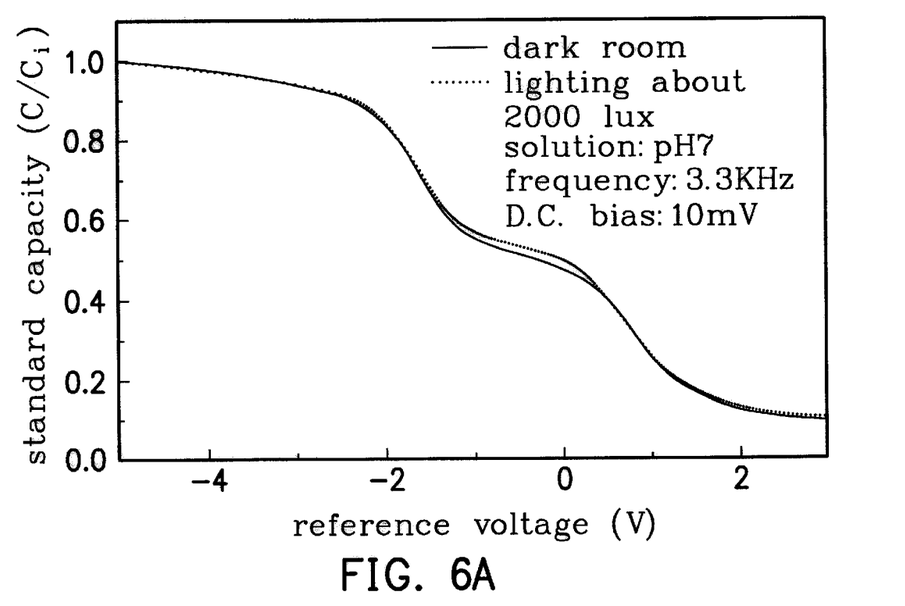
FIG. 6A shows the capacitance-voltage characteristics of the preferred embodiment according to the invention.

Refer to FIG. 6A, which shows the comparison of the characteristic curves of the capacitance-voltage in a dark room and in a room lit with twenty-fold the general intensity of normal room light according to the present invention. Compared with FIG. 6A, the characteristic curves of FIG. 6B in a dark room and in a lit room for the conventional ion sensitive field effect transistor obviously don't match in the range of −3.5~0 volts for the reference voltage.

Figure 6B:
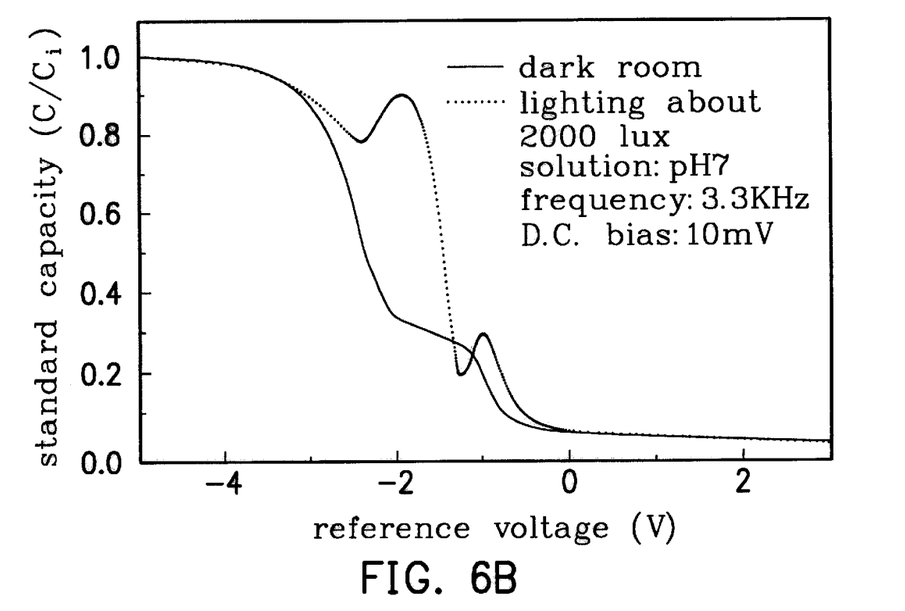
FIG. 6B shows the capacitance-voltage characteristics of the conventional ion sensitive field effect transistor.

Accordingly, light doesn't affect the characteristics of the interface between the solution and the sensing membrane of the ion sensitive field effect transistor with a multi-metal thin film as a light shielding layer of the present invention.

Figure 7:
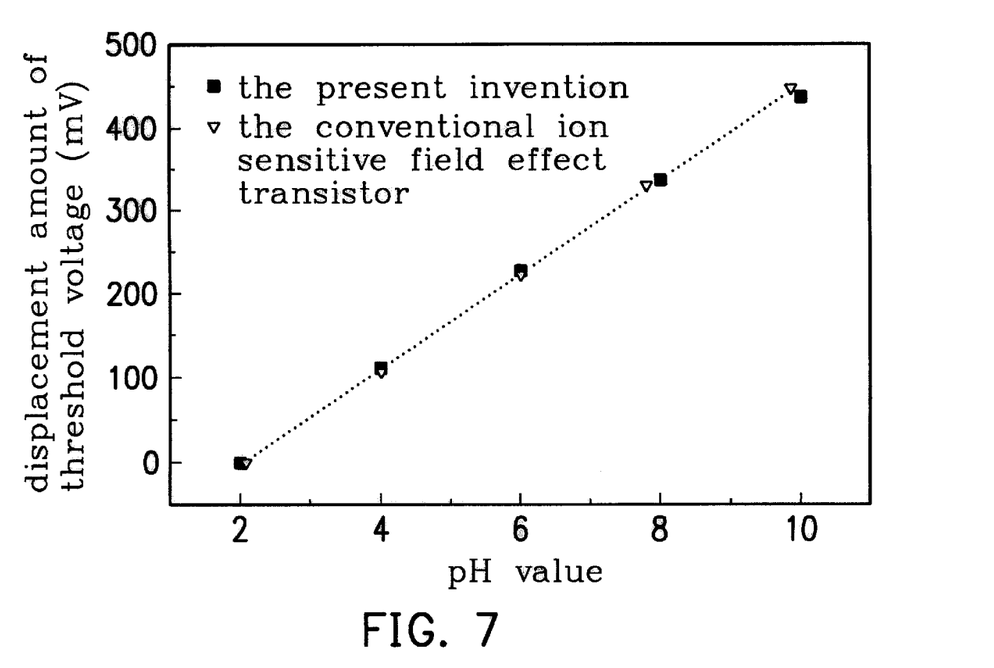
FIG. 7 shows the comparison of the sensing characteristic curves of the conventional ion sensitive field effect transistor and the present invention.

Referring to FIG. 7, the comparison of sensing characteristic curves of the conventional ion sensitive field effect transistor and the present invention are shown. As the displacement amount of threshold voltage of the present invention is similar to that of the conventional ion sensitive field effect transistor, it is evident that the sensing characteristics of the present invention are not changed by the addition of the metal shielding layer.

While the present invention has been described and illustrated herein with reference to the preferred embodiment thereof, it will be understood by those skilled in the art that various changes in form and details may be made therein without departing from the spirit and the scope of the invention.

What is claimed is:

1. An ion sensitive transistor, comprising:
    a semiconductor substrate;
    a pair of source/drains formed in the semiconductor substrate and isolated from each other;
    a gate dielectric layer formed on the surface of the semiconductor between the source and the drain;
    a barrier formed on the surface of the dielectric layer;
    a metal layer formed on the surface of said barrier; and
    a $SnO_x$ layer formed on the surface of the metal layer.

2. The ion sensitive transistor as claimed in claim 1, wherein the gate dielectric layer is a $SiO_x$ layer.

3. The ion sensitive transistor as claimed in claim 1, wherein the barrier is a $Si_3N_4$ layer.

4. The ion sensitive transistor as claimed in claim 1, further comprising epoxy resin for packaging the ion sensitive transistor except for the $SnO_x$ layer.

5. An ion sensitive transistor comprising:
    a semiconductor substrate;
    a source element and a drain element formed in the semiconductor substrate and isolated from each other;
    a dielectric gate layer formed on the surface of the semiconductor substrate between the source element and the drain element;
    a conductive light shielding layer formed above the dielectric gate layer to isolate the dielectric gate layer from the effect of light; and
    a $SnO_x$ layer formed on the surface of the light shielding layer to form a sensing membrane capable of sensing the ion concentration.

6. The ion sensitive transistor of claim 5 wherein the light shielding layer is aluminum and the $SnO_x$ layer is $S_nO_2$.

7. An ion sensitive transistor comprising:

a semiconductor substrate;

a source element and a drain element formed in the semiconductor substrate and isolated from each other;

an insulating layer formed above the source element and the drain element;

a dielectric gate layer formed on the insulating layer and connected to the source element and the drain element;

a conductive light shielding layer formed above the dielectric gate layer to isolate the dielectric gate layer from the effect of light; and an ion sensing layer formed on the surface of the light shielding layer.

8. The ion sensitive transistor of claim 5 wherein the light shielding layer is aluminum and the ion sensing layer is $S_nO_2$.

9. The ion sensitive transistor of claim 8 wherein the dielectric gate layer is $Si_3N_4$.

10. The ion sensitive transistor of claim 9 wherein the transistor is encapsulated in an epoxy resin except for the ion sensing layer.

* * * * *